United States Patent
Kawazoe

(10) Patent No.: US 8,748,605 B2
(45) Date of Patent: Jun. 10, 2014

(54) METHOD FOR PRODUCING 4,6-DIALKOXY-2-CYANOMETHYLPYRIMIDINE AND SYNTHETIC INTERMEDIATE THEREOF

(75) Inventor: Kentaro Kawazoe, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/387,812

(22) PCT Filed: Aug. 4, 2010

(86) PCT No.: PCT/JP2010/004899
§ 371 (c)(1), (2), (4) Date: Mar. 29, 2012

(87) PCT Pub. No.: WO2011/016228
PCT Pub. Date: Feb. 10, 2011

(65) Prior Publication Data
US 2012/0190851 A1  Jul. 26, 2012

(30) Foreign Application Priority Data
Aug. 7, 2009  (JP) .................................. 2009-183939

(51) Int. Cl.
*C07D 239/02* (2006.01)
*C07D 239/52* (2006.01)

(52) U.S. Cl.
CPC .................................. C07D 239/52 (2013.01)
USPC ....................................................... 544/319

(58) Field of Classification Search
CPC .................................................... C07D 239/52
USPC ....................................................... 544/319
See application file for complete search history.

(56) References Cited

FOREIGN PATENT DOCUMENTS

WO  WO-95/25730 A1  9/1995

OTHER PUBLICATIONS

CAS Document Accession No. 2010:146543 (Feb. 10, 2009) (English-language abstract of P. Du et al., 32 Huaxue Shiji 91-93 (2010)).*

P. Du et al., 32 Huaxue Shiji 91-93 (2010).*
P. P Du et al., 32 Huaxue Shiji 91-93 (2010), English-language abstract: CAS Document Accession No. 2010:146543 (Feb. 10, 2009).*
V. Lapachev et al., 11 Inst. Org. Khim., Novosibirsk, USSR: Izvestiya Akademii Nauk SSSR, Seriya Khimicheskaya, 2633-2634 (1977).*
V. Lapachev et al., 6 Novosib. Inst. Org. Khim., Novosibirsk, 630090, USSR Khimiya Geterotsiklicheskikh Soedinenii 827-831 (1984).*
V. Lapachev et al., 6 Khimiya Geterotsiklicheskikh Soedinenii 676-680 (1984).*
Fischer, G.M., et al, Pyrrolopyrrole cyanine dyes . . . and fluorophores, Chemistry-A European Journal, Mar. 18, 2009, vol. 15, No. 19, pp. 4857-4864.

* cited by examiner

*Primary Examiner* — Deepak Rao
*Assistant Examiner* — Alexander R Pagano
(74) *Attorney, Agent, or Firm* — Bacon & Thomas, PLLC

(57) ABSTRACT

Disclosed is a method for producing 4,6-dialkoxy-2-cyanomethylpyrimidine and also disclosed is a synthetic intermediate thereof. More specifically disclosed is a method for producing 4,6-dialkoxy-2-cyanomethylpyrimidine represented by general formula (2) (wherein R represents an alkyl group), comprising reacting a t-butyl cyanoacetate derivative represented by general formula (1) (wherein R has the same meaning as described above) in the presence of an acid, and also disclosed is a t-butyl cyanoacetate derivative represented by general formula (1) (wherein R represents an alkylgroup).

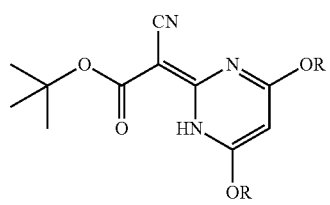

(1)

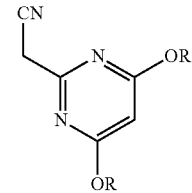

(2)

4 Claims, No Drawings

METHOD FOR PRODUCING 4,6-DIALKOXY-2-CYANOMETHYLPYRIMIDINE AND SYNTHETIC INTERMEDIATE THEREOF

TECHNICAL FIELD

The present invention relates to a method for producing a 4,6-dialkoxy-2-cyanomethylpyrimidine and an intermediate for synthesis of the compound.

BACKGROUND ART

It is known that 4,6-dialkoxy-2-cyanomethylpyrimidine is an intermediate for herbicide synthesis (reference is made to Patent Literatures 1 and 2). For production of this 4,6-dialkoxy-2-cyanomethylpyrimidine, there is known a method of reacting a cyanoacetic acid ester with a 4,6-disubstituted-2-methylsulfonylpyrmidine in the presence of a base to obtain a 2-cyano-2-(4,6-disubstituted pyrimidin-2-yl)acetic acid ester and then subjecting the ester to hydrolysis at 150° C. and subsequent decarboxylation in an aprotic solvent in the presence of 2 equivalents of water and a catalytic amount of an inorganic salt such as sodium chloride or the like (reference is made to Patent Literature 1). This method, however, has had problems in that a high temperature of 150° C. is required and the yield is low at 50 to 60%.

There is also known a method of reacting 2-chloromethyl-4,6-dimethoxypyrimidine with sodium cyanate (reference is made to Patent Literature 2). However, this method is also low (58%) in yield and is not suitable for industrial application.

Thus, there has been known, for production of 4,6-dialkoxy-2-cyanomethylpyrimidine, no method utilizing the high reactivity of tert-butyl 2-cyano-2-(4,6-dialkoxypyrimidin-2-yl)acetate in the presence of an acid. This tert-butyl 2-cyano-2-(4,6-dialkoxypyrimidin-2-yl)acetate is a novel compound not described specifically in the Patent Literatures 1 and 2.

PRIOR ART LITERATURES

Patent Literatures

Patent Literature 1: WO 95/25730
Patent Literature 2: JP-A-1990-282371

SUMMARY OF THE INVENTION

Task to be Achieved by the Invention

The present invention has been made in order to solve the above-mentioned problems of the prior art and provide a method for producing a 4,6-dialkoxy-2-cyanomethylpyrimidine, which is suitable for industrial application, and an intermediate for synthesis of the compound.

Means for Achieving the Task

In view of the above situation, the present inventor made a study on the method for producing a 4,6-dialkoxy-2-cyanomethylpyrimidine. As a result, it was unexpectedly found that the above task could be achieved by reacting tert-butyl cyanoacetate with a 4,6-dialkoxy-2-methanesulfonylpyrimidine in the presence of a base to obtain a tert-butyl 2-cyano-2-(4,6-dialkoxypyrimidin-2-yl)acetate and then subjecting the compound to deprotection in which isobutene and carbon dioxide are generated, or hydrolysis and subsequent decarboxylation. This finding has led to the completion of the present invention.

The present invention has achieved the above task by providing the inventions described in the following [1] to [4].

[1] A method for producing a 4,6-dialkoxy-2-cyanomethylpyrimidine represented by the following general formula (2)

[formula 2]

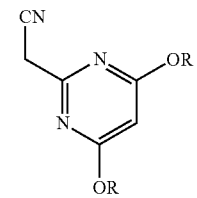

(2)

(wherein R is an alkyl group), which comprises reacting a tert-butyl cyanoacetate derivative represented by the following general formula (1)

[formula 1]

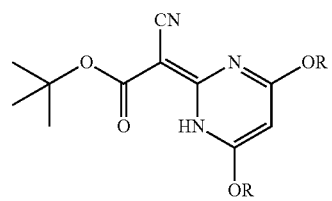

(1)

(wherein R has the same meaning as given above), in the presence of an acid.

[2] A method for producing a 4,6-dialkoxy-2-cyanomethylpyrimidine, according to [1], wherein the reaction in the presence of an acid is deprotection in which isobutene and carbon dioxide are generated, or hydrolysis and decarboxylation.

[3] A method for producing a 4,6-dialkoxy-2-cyanomethylpyrimidine, according to [1], wherein the tert-butyl cyanoacetate derivative represented by the following general formula (1)

[formula 3]

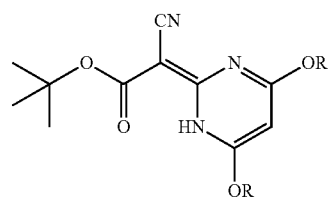

(1)

(wherein R is an alkyl group) is produced by reacting tert-butyl cyanoacetate with a 4,6-dialkoxy-2-methanesulfonylpyrimidine represented by the following general formula (3)

[formula 4]

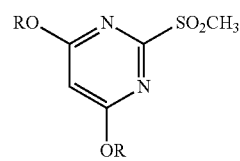

(3)

(wherein R has the same meaning as given above).

[4] A tert-butyl cyanoacetate derivative represented by the following general formula (1)

[formula 5]

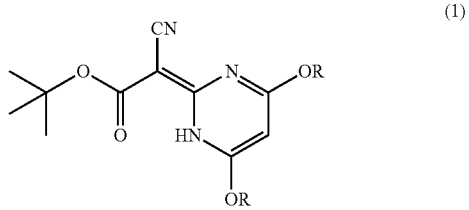

(1)

(wherein R is an alkyl group).

Effect of the Invention

The present invention provides a novel method for producing a 4,6-dialkoxy-2-cyanomethylpyrimidine industrially. With the present method, an intended 4,6-dialkoxy-2-cyanomethylpyrimidine can be produced with raw materials of good availability, without using any special reactor and under mild conditions, at a high selectivity, efficiently, and in a simple operation.

BEST MODE FOR CARRYING OUT THE INVENTION

The present invention is described in detail below.

The present invention lies in a tert-butyl cyanoacetate derivative represented by the general formula (1) and a method for producing a 4,6-dialkoxy-2-cyanomethylpyrimidine represented by the general formula (2), by using the derivative. The present invention is based on the high reactivity of the tert-butyl ester in the tert-butyl cyanoacetate derivative with an acid, and the derivative should be distinguished from other alkyl ester derivative such as ethyl ester derivative (reference is made to Comparative Example 1).

Then, description is made on the tert-butyl cyanoacetate derivative represented by the general formula (1).

In the tert-butyl cyanoacetate derivative represented by the general formula (1), there is, as shown in the following formula

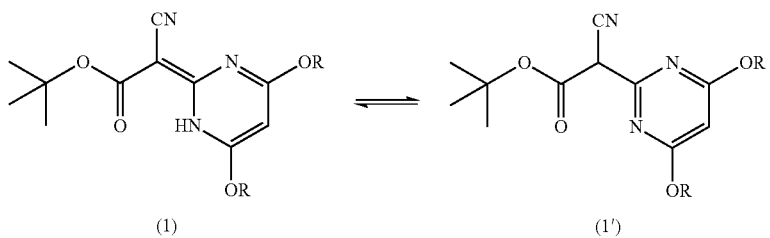

[formula 6]

(wherein R has the same meaning as give above) a tautomer, i.e. a tert-butyl 2-cyano-2-(4,6-dialkoxypyrimidin-2-yl)acetate represented by the general formula (1'). In the present description, the specific name of the tert-butyl cyanoacetate derivative represented by the general formula (1) is mentioned and described based on the structure of its corresponding tautomer, i.e. the tert-butyl 2-cyano-2-(4,6-dialkoxypyrimidin-2-yl)acetate represented by the general formula (1').

Incidentally, R in the tert-butyl cyanoacetate derivative represented by the general formula (1) has the same meaning as give above and is a lower alkyl group of 1 to 6 carbon atoms such as methyl group, ethyl group, n-propyl group, isopropyl group, n-butyl group, sec-butyl group, tert-butyl group, n-pentyl group, n-hexyl group or the like, or a cyclic lower alkyl group such as cyclopropyl group, cyclobutyl group, cyclopentyl group, cyclohexyl group or the like.

Therefore, as specific examples of the tert-butyl cyanoacetate derivative represented by the general formula (1), there can be mentioned tert-butyl 2-cyano-2-(4,6-dimethoxypyrimidin-2-yl)acetate, tert-butyl 2-cyano-2-(4,6-diethoxypyrimidin-2-yl)acetate, tert-butyl 2-cyano-2-(4,6-di-n-propoxypyrimidin-2-yl)acetate, tert-butyl 2-cyano-2-(4,6-di-isopropoxypyrimidin-2-yl)acetate, tert-butyl 2-cyano-2-(4,6-di-n-butoxypyrimidin-2-yl)acetate, tert-butyl 2-cyano-2-(4,6-di-sec-butoxypyrimidin-2-yl)acetate, tert-butyl 2-cyano-2-(4,6-di-tert-butoxypyrimidin-2-yl)acetate, tert-butyl 2-cyano-2-(4,6-di-n-pentyloxypyrimidin-2-yl)acetate, tert-butyl 2-cyano-2-(4,6-di-n-hexyloxypyrimidin-2-yl)acetate, tertbutyl 2-cyano-2-(4,6-dicyclopropoxypyrimidin-2-yl)acetate, tert-butyl 2-cyano-2-(4,6-dicyclobutoxypyrimidin-2-yl)acetate, tert-butyl 2-cyano-2-(4,6-dicyclopentyloxypyrimidin-2-yl)acetate, and tert-butyl 2-cyano-2-(4,6-dicyclohexyloxypyrimidin-2-yl)acetate.

Next, description is made on the method for producing a 4,6-dialkoxy-2-cyanomethylpyrimidine represented by the general formula (2).

The 4,6-dialkoxy-2-cyanomethylpyrimidine represented by the general formula (2) can be produced by reacting a tert-butyl cyanoacetate derivative represented by the general formula (1) with an acid to give rise to deprotection in which isobutene and carbon dioxide are generated, or to hydrolysis and decarboxylation.

The acid used in the reaction may be any acid as long as the reaction takes place. As specific examples, there can be mentioned sulfonic acids including aliphatic sulfonic acids such as methanesulfonic acid and the like and aromatic sulfonic acids such as p-toluenesulfonic acid, benzenesulfonic acid, p-chlorobenzenesulfonic acid and the like; mineral acids such as hydrochloric acid, sulfuric acid, nitric acid and the like; carboxylic acids such as formic acid, acetic acid, trifluoroacetic acid and the like; Lewis acids such as boron trifluoride-tetrahydrofuran (THF) complex, aluminum chloride, zinc chloride and the like; and solid acids such as montmorillonite K-10 and the like. As the acid used in the reaction, preferred are sulfonic acids such as methanesulfonic acid, p-toluenesulfonic acid and the like, mineral acids such as hydrochloric acid, sulfuric acid, nitric acid and the like, and carboxylic acids such as formic acid, acetic acid, trifluoroacetic acid and the like, from the standpoints of good availability and handleability, reactivity, etc.; and more preferred are sulfonic acids such as methanesulfonic acid, p-toluenesulfonic acid and the like, and mineral acids such as hydrochloric acid, sulfuric acid, nitric acid and the like. These acids may be used singly, or in two or more kinds at any proportions.

As to the molar ratio of the acid used in the reaction, the reaction proceeds at any molar ratio relative to the tert-butyl cyanoacetate derivative represented by the general formula (1). However, the acid is used ordinarily in an amount of, for example, 0.01 to 100.0 moles, preferably 0.1 to 20.0 moles, more preferably 0.2 to 10.0 moles, relative to the molar ratio 1 mole of the tert-butyl cyanoacetate derivative represented by the general formula (1).

The reaction may be carried out using no solvent. However, a solvent is preferably used for smooth progress of the reaction. The solvent used in the reaction may be any solvent as long as it does not inhibit the reaction. There can be mentioned, for example, aromatic hydrocarbons such as toluene, xylene, chlorobenzene and the like; aprotic polar solvents such as N,N-dimethylformamide (DMF), N,N-dimethylacetamide (DMAC), acetonitrile, propylene carbonate and the like; ethers such as phenyl ether, tetrahydrofuran (THF) and the like; halogen-containing solvents such as dichloromethane and the like; alcohols such as methanol, ethanol, isopropanol, ethylene glycol and the like; water; and aliphatic hydrocarbons such as pentane, n-hexane and the like. Use of an aromatic hydrocarbon such as toluene, xylene or the like is preferred and use of toluene is preferred particularly.

The solvents may be used singly or in mixed solvent of any mixing proportions.

The amount of the solvent used may be any amount as long as it allows sufficient stirring of the reaction system. However, the solvent is used in an amount of ordinarily 0 to 10 liters, preferably 0.2 to 2 liters relative to one mol of the tert-butyl cyanoacetate derivative represented by the general formula (1).

The temperature of the reaction may be, for example, a range of 0° C. to the refluxing temperature of the solvent used, but is preferably a range of 10 to 100° C.

The time of the reaction is not particularly restricted but is preferably 1 to 30 hours from the standpoints of, for example, the prevention of by-product formation.

Then, description is made on the 4,6-dialkoxy-2-cyanomethylpyrimidine represented by the general formula (2), which is produced by the present invention method.

The group R in the general formula (2) of 4,6-dialkoxy-2-cyanomethylpyrimidine has the same meaning as given above.

Therefore, as specific examples of the 4,6-dialkoxy-2-cyanomethylpyrimidine represented by the general formula (2), there can be mentioned 2-cyanomethyl-4,6-dimethoxypyrimidine, 2-cyanomethyl-4,6-diethoxypyrimidine, 2-cyanomethyl-4,6-di-n-propoxypyrimidine, 2-cyanomethyl-4,6-diisopropoxypyrimidine, 4,6-di-n-butoxy-2-cyanomethylpyrimidine, 4,6-di-sec-butoxy-2-cyanomethylpyrimidine, 4,6-di-tert-butoxy-2-cyanomethylpyrimidine, 2-cyanomethyl-4,6-di-n-pentyloxypyrimidine, 2-cyanomethyl-4,6-di-n-hexyloxypyrimidine, 2-cyanomethyl-4,6-dicyclopropoxypyrimidine, 2-cyanomethyl-4,6-dicyclopropoxypyrimidine, 2-cyanomethyl-4,6-dicyclobutoxypyrimidine, 2-cyanomethyl-4,6-dicyclopentyloxypyrimidine, and 2-cyanomethyl-4,6-dicyclohexyloxypyrimidine.

Then, description is made on the method for producing a tert-butyl cyanoacetate derivative represented by the general formula (1), which is a raw material in the present invention method.

The tert-butyl cyanoacetate derivative represented by the general formula (1) can be produced by reacting tert-butyl cyanoacetate with a 4,6-dialkoxy-2-methanesulfonylpyrimidine represented by the general formula (3). Incidentally, the tert-butyl cyanoacetate is a known compound.

The group R in the general formula 3) of 4,6-dialkoxy-2-methanesulfonylpyrimidine has the same meaning as given above.

Therefore, as specific examples of the 4,6-dialkoxy-2-methanesulfonylpyrimidine represented by the general formula (3), there can be mentioned 4,6-dimethoxy-2-methanesulfonylpyrimidine, 4,6-diethoxy-2-methanesulfonylpyrimidine, 4,6-di-n-propoxy-2-methanesulfonylpyrimidine, 4,6-diisopropoxy-2-methanesulfonylpyrimidine, 4,6-di-n-butoxy-2-methanesulfonylpyrimidine, 4,6-di-sec-butoxy-2-methanesulfonylpyrimidine, 4,6-di-tert-butoxy-2-methanesulfonylpyrimidine, 2-methanesulfonyl-4,6-di-n-pentanoxypyrimidine, 4,6-di-n-hexanoxy-2-methanesulfonylpyrimidine, 4,6-dicyclopropoxy-2-methanesulfonylpyrimidine, 4,6-dicyclobutoxy-2-methanesulfonylpyrimidine, 4,6-dicyclopentanoxy-2-methanesulfonylpyrimidine, and 4,6-dicyclohexanoxy-2-methanesulfonylpyrimidine.

The molar ratio of the tert-butyl cyanoacetate and the 4,6-dialkoxy-2-methanesulfonylpyrimidine represented by the general formula (3), both used in the reaction may be any molar ratio and the reaction proceeds satisfactorily. However, the use amount of the 4,6-dialkoxy-2-methanesulfonylpyrimidine represented by the general formula (3) may be, for example, ordinarily 0.1 to 10.0 mols, preferably 0.5 to 2.0 mols, more preferably 0.8 to 1.2 mols relative to 1 mol of the tert-butyl cyanoacetate.

The reaction may be conducted using no base. However, use of base is preferred for smooth progress of the reaction. As specific examples of the base used in the reaction, there can be mentioned inorganic bases such as potassium carbonate, sodium carbonate, potassium hydrogencarbonate, sodium hydrogencarbonate, potassium hydroxide, sodium hydroxide and the like; and tertiary amine compounds such as pyridine, N,N-diisopropylethylamine, triethylamine and the like. These bases may be used singly or in admixture of any proportions. Inorganic bases such as potassium carbonate, sodium carbonate, potassium hydrogencarbonate, sodium hydrogencarbonate, potassium hydroxide, sodium hydroxide and the like are preferably used from the standpoints of good availability and handleability, reactivity, etc., and potassium carbonate and sodium carbonate are used more preferably.

The molar ratio of the base used in the reaction may be any molar ratio relative to the tert-butyl cyanoacetate and the reaction proceeds satisfactorily. However, the use amount of the base may be, for example, ordinarily 0 to 10.0 mols, preferably 0.33 to 3.0 mols, more preferably 1.5 to 2.5 mols relative to 1 mol of the tert-butyl cyanoacetate.

The reaction may be conducted using no solvent. However, use of solvent is preferred for smooth progress of the reaction. The solvent used in the reaction may be any solvent as long as it does not inhibit the reaction. There can be mentioned, for example, aprotic polar solvents such as N,N-dimethylformamide (DMF), N,N-dimethylacetamide (DMAC), acetonitrile, propylene carbonate and the like; alcohols such as methanol, ethanol, isopropanol, ethylene glycol and the like; aromatic hydrocarbons such as toluene, xylene, chlorobenzene and the like; ethers such as phenyl ether, tetrahydrofuran (THF) and the like; halogen-containing solvents such as dichloromethane and the like; and aliphatic hydrocarbons such as pentane, n-hexane and the like. Preferably used are alcohols such as methanol, ethanol, isopropanol, ethylene glycol and the like, or aprotic polar solvents such as N,N-dimethylformamide (DMF), N,N-dimethylacetamide (DMAC), acetonitrile, propylene carbonate and the like; more preferably used are aprotic polar solvents such as N,N-dimethylformamide (DMF), N,N-dimethylacetamide (DMAC), acetonitrile, propylene carbonate and the like; particularly preferably used is N,N-dimethylformamide (DMF).

The solvents can be used singly or in admixture of any mixing proportions.

The amount of the solvent used may be any amount as long as it allows sufficient stirring of the reaction system. However, the solvent is used in an amount of ordinarily 0 to 10 liters, preferably 0.2 to 2 liters relative to one mol of tert-butyl cyanoacetate.

The temperature of the reaction may be, for example, a range of 0° C. to the refluxing temperature of the solvent used, but is preferably a range of 10 to 100° C.

The time of the reaction is not particularly restricted but is preferably 1 to 30 hours from the standpoints of, for example, the prevention of by-product formation.

Incidentally, the 4,6-dialkoxy-2-methanesulfonylpyrimidine represented by the general formula (3) is a known compound, or can be produced, for example, by reacting diethyl malonate with thiourea and then giving rise to methylation of mercapto group, chlorination of hydroxyl group, alkoxylation of chloro group, and oxidation of methyl sulfide group.

According to the present invention, by using, as a raw material, a tert-butyl cyanoacetate derivative represented by the general formula (1) which can be easily produced from tert-butyl cyanoacetate and a 4,6-dialkoxy-2-methanesulfonylpyrimidine represented by the general formula (3), an intended 4,6-dialkoxy-2-cyanomethylpyrimidine represented by the general formula (2) can be produced without using any special reactor and under mild conditions, at a high selectivity, efficiently and in a simple operation. The 4,6-dialkoxy-2-cyanomethylpyrimidine represented by the general formula (2) is a compound which is useful as an intermediate for herbicide synthesis.

EXAMPLES

Next, the method for producing the present invention compound is described specifically below by way of examples. However, the present invention is in no way restricted by these examples.

Example 1

A: Production of tert-butyl 2-cyano-2-(4,6-dimethoxypyrimidin-2-yl)acetate

Into a 100-ml eggplant-shaped flask equipped with a magnetic stirrer and a reflux condenser were added 6.08 g (44 mmol) of potassium carbonate, 4.36 g (20 mmol) of 2-methanesulfonyl-4,6-dimethoxypyrimidine, 3.11 g (22 mmol) of tert-butyl cyanoacetate and 10 ml of N,N-dimethylformamide. The system inside was purged with nitrogen and stirred for 2 hours at 60° C. and for 4 hours at 70° C. The reaction slurry was cooled to room temperature and poured into 30 ml of a 5% aqueous hydrochloric acid solution. Thereto was added 50 ml of water, and concentrated hydrochloric acid was dropped until the system became acidic, followed by sufficient stirring. Then, filtration and washing with 30 ml of water were conducted. The crystals obtained were dried to obtain tert-butyl 2-cyano-2-(4,6-dimethoxypyrimidin-2-yl)acetate as white crystal of 5.4 g. HPLC purity: 99.3% Yield: 97%

Decomposition point: 188° C.
$^1$H-NMR (300 MHz, CDCl$_3$) δ:
13.24 (br, 1H), 5.35 (d, J=2.1 Hz, 1H), 4.04 (s, 3H), 3.94 (s, 3H), 1.53 (s, 9H) ppm

LC-MS (M+1) 280.1

B: Production of 2-cyanomethyl-4,6-dimethoxypyrimidine

Into a 50-ml eggplant-shaped flask provided with a magnetic stirrer and a reflux condenser were added 2.79 g (10 mmol) of tert-butyl 2-cyano-2-(4,6-dimethoxypyrimidin-2-yl)acetate, 10 ml of toluene and then 0.38 g (4 mmol) of methanesulfonic acid. The system inside was purged with nitrogen and stirred for 2 hours at 100° C. After the completion of a reaction, the system was cooled to room temperature; 30 ml water and 30 ml of ethyl acetate were added for phase separation; and re-extraction was conducted using 20 ml of ethyl acetate. Two ethyl acetate phases were combined, washed with saturated sodium chloride water, and dried over anhydrous sodium sulfate. Then, ethyl acetate was distilled off under reduced pressure to obtain 2-cyanomethyl-4,6-dimethoxypyrimidine as white crystal of 1.45 g. HPLC purity: 95.7% Yield: 81%

Melting point: 71 to 72° C.
$^1$H-NMR (300 MHz, CDCl$_3$) δ: 5.97 (s, 1H), 3.96 (s, 6H), 3.88 (s, 2H) ppm

LC-MS (M+1)=180.4

Example 2

The Invention Described in [1]

Production of 2-cyanomethyl-4,6-dimethoxypyrimidine

Into a 15-ml test tube-type reactor provided with a magnetic stirrer and a reflux condenser were added 0.28 g (1 mmol) of tert-butyl 2-cyano-2-(4,6-dimethoxypyrimidin-2-yl)acetate, 1 ml of toluene and 0.5 g (5 mmol) of 35% hydrochloric acid, followed by stirring for 5 hours at 100° C. In this case, the reaction mixture contained 84.0% of 2-cyanomethyl-4,6-dimethoxypyrimidine in terms of the areal ratio of HPLC (UV: 254 nm) excluding toluene.

LC-MS (M+1)$^+$=180.4

Comparative Example 1

Production of 2-cyanomethyl-4,6-dimethoxypyrimidine

Into a 15-ml test tube-type reactor provided with a magnetic stirrer and a reflux condenser were added 0.25 g (1 mmol) of ethyl 2-cyano-2-(4,6-dimethoxypyrimidin-2-yl)acetate, 1 ml of toluene and 0.04 g (0.4 mmol) of methanesulfonic acid, followed by stirring for 3.5 hours at 100° C. In this case, the reaction mixture contained 0.9% of 2-cyanomethyl-4,6-dimethoxypyrimidine in terms of the areal ratio of HPLC (UV: 254 nm) excluding toluene, and there remained 59.2% of ethyl 2-cyano-2-(4,6-dimethoxypyrimidin-2-yl)acetate which was a raw material.

Comparative Example 2

Production of 2-cyanomethyl-4,6-dimethoxypyrimidine (the production method of Patent Literature 1)

436 g (2 mol) of 2-methanesulfonyl-4,6-dimethoxypyrimidine and 218 g (2.2 mol) of methyl cyanoacetate were dissolved in 2.0 liters of N,N-dimethylformamide. Thereto was gradually added 304 g (2.2 mol) potassium carbonate at 80° C., followed by stirring for 3 hours at the same temperature. The reaction mixture was poured into ice water and the whole mixture was made acidic (pH=1) using concentrated hydrochloric acid, followed by stirring for 1 hour. The precipitate (crystals) was separated by filtration and washed by water. The hydrated methyl 2-cyano-2-(4,6-dimethoxypyrimidin-2-yl)acetate obtained was suspended in 1.5 liters of dimethyl sulfoxide, followed by stirring for 3 hours at 150° C. The reaction mixture was cooled to room temperature and poured into water. The precipitate (crystals) was separated by filtration, water-washed, and dried. 2-Cyanomethyl-4,6-dimethoxypyrimidine was obtained at a 60% yield.

INDUSTRIAL APPLICABILITY

The present invention provides a novel method for industrial production of 4,6-dialkoxy-2-cyanomethylpyrimidine. With the present invention method, by using, as a raw material, a tert-butyl cyanoacetate derivative represented by the general formula (1) which can be easily produced from tert-butyl cyanoacetate of the good availability, and a 4,6-dialkoxy-2-methanesulfonylpyrimidine represented by the general formula (3), an intended 4,6-dialkoxy-2-cyanomethylpyrimidine represented by the general formula (2) can be produced without using any special reactor and under mild conditions, at a high selectivity, efficiently, and in a simple operation. Moreover, the present invention method generates no harmful waste derived from catalyst or transition metal, accordingly is easy in waste disposal and friendly to environment, and has a high industrial value.

The invention claimed is:

1. A method for producing a 4,6-dialkoxy-2-cyanomethylpyrimidine represented by the following general formula (2)

[formula 2]

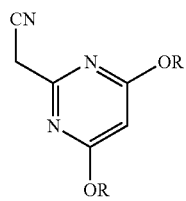

(2)

(wherein R is an alkyl group), which comprises reacting a tert-butyl cyanoacetate derivative represented by the following general formula (1)

[formula 1]

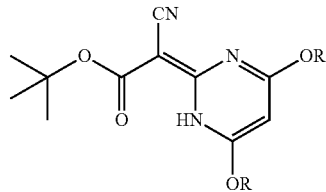

(1)

(wherein R has the same meaning as given above), in the presence of an acid.

2. A method for producing a 4,6-dialkoxy-2-cyanomethylpyrimidine, according to claim 1, wherein the reaction in the presence of an acid is deprotection in which isobutene and carbon dioxide are generated, or hydrolysis and decarboxylation.

3. A method for producing a 4,6-dialkoxy-2-cyanomethylpyrimidine, according to claim 1, wherein the tert-butyl cyanoacetate derivative represented by the following general formula (1)

[formula 3]

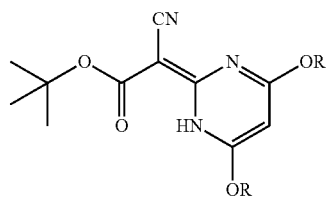

(1)

(wherein R is an alkyl group) is produced by reacting tert-butyl cyanoacetate with a 4,6-dialkoxy-2-methanesulfonylpyrimidine represented by the following general formula (3)

[formula 4]

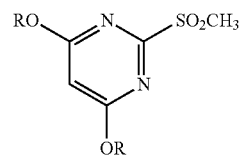

(3)

(wherein R has the same meaning as given above).

4. A tert-butyl cyanoacetate derivative represented by the following general formula (1)

[formula 5]

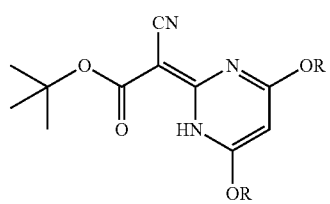

(1)

(wherein R is an alkyl group).

* * * * *